United States Patent

Fürstner et al.

Patent Number: 5,936,100
Date of Patent: Aug. 10, 1999

[54] SYNTHESIS OF FUNCTIONALIZED MACROCYCLES BY RING CLOSING METATHESIS

[75] Inventors: Alois Fürstner; Klaus Langemann; Nicole Kindler, all of Mülheim an der Ruhr, Germany

[73] Assignee: Studiengesellschaft Kohle MBH, Mulheim an der Ruhr, Germany

[21] Appl. No.: 08/767,561

[22] Filed: Dec. 16, 1996

[51] Int. Cl.⁶ ............. C07D 313/00; C07D 49/587; C07C 45/65
[52] U.S. Cl. ............. 549/266; 540/451; 540/467; 549/346; 568/349; 568/375
[58] Field of Search ............. 549/266; 568/349, 568/375

[56] References Cited

PUBLICATIONS

Tsuji et al, Tet. Letters, vol. 21, pp. 2955–2958, 1980.
Junga et al, Tet. Letters, vol. 34(23), pp. 3731–3732, 1993.
Furstner et al., J. Org. Chem., vol. 61(12), pp. 3942–3943, Jun. 1996.
Nicolaou et al, Angew. Chem. Int. Ed. Engl., vol. 35(20), pp. 2399–2401, Nov. 1996.
Furstner et al, Tet. Letters, vol. 37 (39), pp. 7005–7008, Oct. 1996.
Houri et al, J. Am. Chem. Soc., vol. 117, pp. 2943–2944, (1995).
Clark et al, J. Am. Chem. Soc., vol. 117, pp. 12364–12365, (1995).
Grubbs et al, Acc. Chem. Res., vol. 28, pp. 446–452, (1995).
Miller et al, J. Am. Chem. Soc., vol. 117, pp. 5855–5856, (1995).
Borer et al, Tet. Letters, vol. 35, pp. 3191–3194, 1994.
König et al, Synlett, pp. 1013–1014, Oct. 1996.
Plugge et al., Synlett, pp. 507–508, Jul. 1991.

*Primary Examiner*—Bernard Dentz
*Attorney, Agent, or Firm*—Sprung Kramer Schaefer & Briscoe

[57] ABSTRACT

The invention concerns an improved process for the preparation of macrocyclic products with 12 or more ring atoms containing one or more polar functional groups on the ring and/or one or more heteroatoms within the ring by ring closing metathesis (RCM) of suitably substituted diene precursors even if the substrates are devoid of any kind of conformational preorganization. Metal carbene complexes of Ru, Mo, W, Re, Os, which are tolerant towards the respective functional group and can either be isolated or prepared in situ are used as catalysts or catalyst precursors. Preferred catalysts or catalyst precursors are ruthenium complexes of the general type $XX_1LL_1Ru=CRR_1$, wherein X, $X_1$=halogen, L, $L_1$=trialkylphosphine, R, R1=H, Ph, $CH=CPh_2$ denote the most preferred embodiment. The process can be applied to the synthesis of olfactory compounds, perfumary ingredients, pheromones, crown ethers, antibiotics and pharmaceuticals for human and veterinary medicine.

19 Claims, No Drawings

SYNTHESIS OF FUNCTIONALIZED MACROCYCLES BY RING CLOSING METATHESIS

BACKGROUND OF THE INVENTION

The invention concerns an improved process for the preparation of macrocyclic products with 12 or more ring atoms containing one or more polar functional groups on the ring and/or one or more heteroatoms within the ring by ring closing metathesis (RCM) of suitably substituted diene precursors, which more specifically can be applied to the synthesis of olfactory compounds, perfumary ingredients, pheromones, crown ethers, antibiotics and pharmaceuticals for human and veterinary medicine.

PRIOR ART

Macrocyclic compounds with ring sizes $x \geq 12$ are difficult to prepare because of the tendency of any appropriate cyclization precursor to undergo competing oligomerization or polymerization reactions [Review: Roxburgh, C. J. *Tetrahedron* 1995, 51, 9767–9822; Illuminati, G. et al., *Acc. Chem. Res.* 1981, 14, 95–102]. However, since macrocycles are very often found as substructures in physiologically active natural products and are commercialized on a large scale e.g. in form of perfumary ingredients, a demand for the development of new and more efficient synthetic approaches persists.

A particularly appealing method for this purpose is ring closing metathesis (RCM) of a suitable diene precursor by means of a transition metal catalyst. Previous work in this area has been limited by the low compatibility of commonly used metathesis catalysts with polar functional groups [Reviews: Ivin, K. J. *Olefin Metathesis*, Academic Press, New York, 1983; Grubbs, R. H. et al., *Science*, 1989, 243, 907–915; Grubbs, R. H. et al. *Comprehensive Organic Synthesis* (Trost, B. M., Fleming, I., Eds), Pergamon, Oxford, 1991, Vol. 5, 1115–1127].

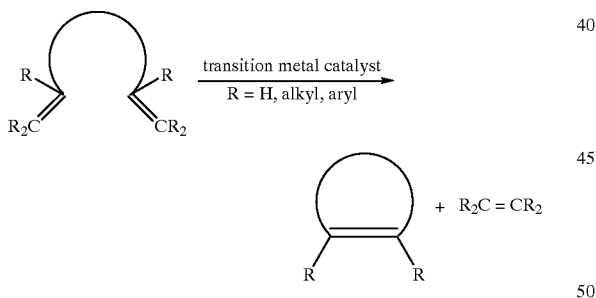

Only recently more tolerant metathesis catalysts or pre-catalysts have been described which turned out to be efficient for the synthesis of 5-, 6-, and 7-membered carbo- and heterocycles. In general, the active species are believed to be metal carbene complexes which are generated in situ from appropriate precursors [Reviews: Grubbs R. H. et al., *Acc. Chem. Res.* 1995, 28, 446–452; Schmalz, H.-G. *Angew. Chem.* 1995, 107, 1981–1984]. Among them, complexes of the general type I (M=Ru, Os) are noteworthy [WO 96/04289, 15.02.1996; Nguyen et al., *J. Am. Chem. Soc.* 1992, 114, 3974–3975; Nguyen et al., *J. Am. Chem. Soc.* 1993, 115, 9858–9859; Schwab, P. et al., *Angew. Chem.* 1995, 107, 2179–2181; Schwab, P. et al. *J. Am. Chem. Soc.* 1996, 118, 100–110; Mohr, B. et al. *Organometallics* 1996, 15, 4317–4325]. Other catalysts or catalyst precursors with similar application profiles comprise molybdenum carbenes of the general type II [Schrock, R. R. *J. Am. Chem. Soc.* 1990, 112, 3875–3886; Fujimura, O. *Organometallics* 1996, 15, 1865–1871], tungsten carbenes of the general type III [Quingnard, F. et al., *J. Mol. Catal.* 1986, 36, 13–29], organorhenium oxide species of the general type IV [Herrmann, W. A. et al. *Angew. Chem.* 1991, 103, 1704–1706], allylruthenium complexes of the general type V [Herrmann, W. A. et al. *Angew. Chem.* 1996, 108, 1169–1170], and mixed metal systems of the general type VI [Nugent, W. A. et al. *J. Am. Chem. Soc.* 1995, 117, 8992–8998].

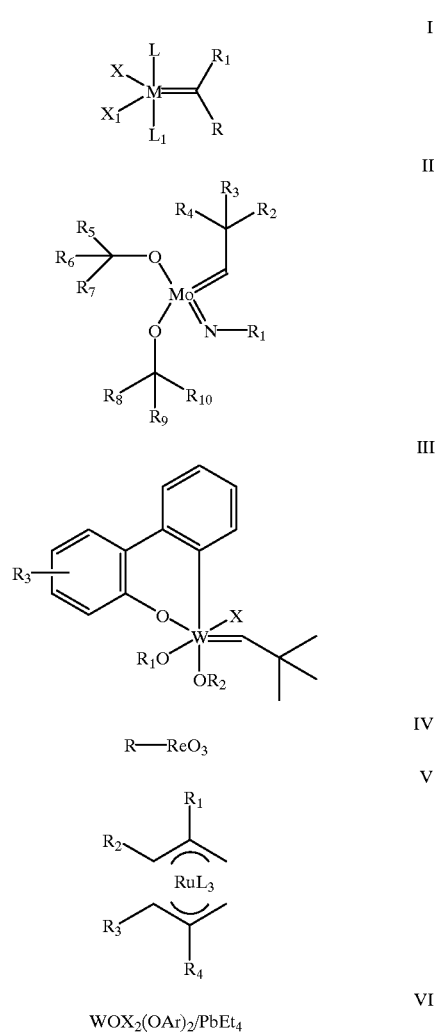

In contrast to the successful use of catalysts I–VI for the synthesis of 6–8 membered rings, their applications to the preparation of functionalized macrocyclic products (ring sizes $x \geq 12$) by RCM of suitable dienes (i) either failed to give cyclic monomers and led only to the recovery and/or to the dimerization or oligomerization of the substrate even under highly dilute reaction conditions. [Martin, S. F. et al., *Tetrahedron* 1996, 52, 7251–7264; Martin, S. F. et al., *Tetrahedron Lett.* 1994, 6005–6008; Forbes, M. D. E. et al., *J. Am. Chem. Soc.* 1992, 114, 10978–10980], or (ii) are very unefficient in terms of yield of the desired product and/or turn-over number of the catalyst, and/or reaction time [Borer, B. C. et al. *Tetrahedron Lett.* 1994, 3191–3194; Plugge, M. F. C. et al., *Synlett* 1991, 507–508; Junga, B. et al. *Tetrahedron Lett.* 1993, 3731–3732]. For example, a dicomponent metathesis catalyst has completely failed in an attempted formation of a macrocyclic ketone by RCM, while >20% of the same catalyst gave only less than 20% yield of macrolactones (i.e. less than 1 turn-over!) [Tsuji et al., *Tetrahedron Lett.* 1980, 2955–2958]. A more recent synthesis of a 14-membered macrolactam is also representative, in which 25 mol % of a molybdenum catalyst of type II have been necessary to achieve a 60% yield of the product (less than 3 turn-overs!), while catalysts of type I have completely failed [Houri, A. F. et al. *J. Am. Chem. Soc.* 1995, 117, 2943–2944], or (iii) were hampered by competing double bond isomerizations during metathesis, which could only be prevented by using specific substrates [Junga, H. et al. *Tetrahedron Lett.* 1993, 3731–3732], or (iv) were successful only with special types of substrates which are conformationally predisposed for ring-closure by different means such as hydrogen bonding, rigified back-bones or supramolecular ensembles [Clark, T. D. et al., *J. Am. Chem. Soc.* 1995, 117, 12364–12365; Miller, S. J. et al., *J. Am. Chem. Soc.* 1995, 117, 5855–5856].

From these results it has been concluded on several occasions that macrocycle syntheses define the limitations of RCM. This is clearly reflected in statements such as "a notable limitation for RCM had proven to be the synthesis of carbocycles and heterocycles of more than seven atoms" [Grubbs, R. H. et al. *Acc. Chem. Res.* 1995, 28, 446–452, see p. 450] or " . . . certain chain length and/or conformations of the diene are necessary for high-yield cyclization" [Forbes, M. D. E. et al., *J. Am. Chem. Soc.* 1992, 114, 10978–10980], or " . . . [das] Gebiet der Macrolidsynthese mag die Grenzen der Methode markieren" ( . . . [the] field of macrolide syntheses may define the limitations of the method) [Koert, U. *Nachr. Chem. Techn. Lab.* 1995, 43, 809–814, see p.812].

In line with these general conclusions, applications of ring closing metathesis (RCM) to the synthesis of saturated or unsaturated macrocyclic lactones or -ketones such as 1,15-pentadecanolide (Exaltolid®), 7-hexadecen- 16-olide (Ambrettolid®), civetone, muscone, cyclopentadecanone (Exalton®), Muscenon® and related compounds which are used as perfumary ingredients [Review: Ohloff, G. *Riechstoffe und Geruchssinn*, Springer, Berlin, 1990] are either unknown, or have been very unefficient [Tsuji, J. et al., *Tetrahedron Lett.* 1980, 2955–2958; Plugge, M. F. C. et al., *Synlett* 1991, 507–508; Junga, H. et al. *Tetrahedron Lett.* 1993, 3731–3732], or made use of heterogeneous catalysts containing undesirable toxic components and high boiling solvents which render the product isolation/purification difficult [Villemin, D. *Tetrahedron Lett.* 1980, 1715–1718; Review: Warwel, R. et al. *Seifen-Öle-Fette-Wachse*, 1989, 115, 538–545].

DETAILED DESCRIPTION OF THE INVENTION

The present invention relates to a process for the synthesis of macrocyclic products ($12 \leq x \leq 30$) containing one or more polar functional groups by ring closing metathesis (RCM) of suitably substituted diene precursors, including substrates which are devoid of any conformational constraints or of other elements of molecular preorganization. Complexes of the general types I–VI are used as catalysts or catalyst-precursors.

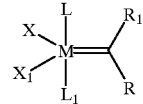

I

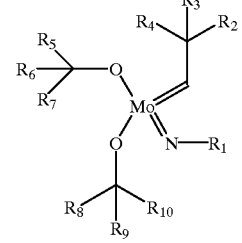

II

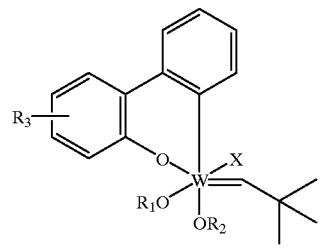

III

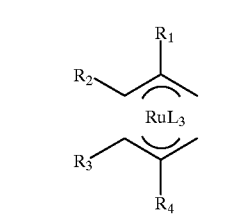

IV

R—ReO$_3$

V

VI

WOX$_2$(OAr)$_2$/PbEt$_4$

The polar functional groups may be substituents on the ring and/or heteroatoms within the macrocyclic structure. This includes esters, ethers, epoxides, silyl ethers, silylketene acetals, thioacetals, acylals, anhydrides, thioethers, imines, silylenol ethers, amines, ammonium salts, amides, nitriles, perfluoroalkyl groups, halogens, alcohols, ketones, aldehydes, carbamates, carbonates, ureas, sulfonates, sulfones, disubstituted alkenes, trisubstituted alkenes, tetrasubstituted alkenes, and nitro groups. The process can be applied to the synthesis of olfactory compounds, perfumary ingredients, pheromones, crown ethers and macrocyclic antibiotics.

The reactions are usually carried out by mixing the solution of the diolefin substrate with the solution of one of the complexes of the general type I–VI as catalyst or catalyst-precursor in a temperature range from about −20° C. to about 125° C., preferably 0° C. to 90° C. The reaction time is not critical and can be from 1 h to several days. The reactions can be conducted in the presence of oxygen. However, it is preferred to carry them out in an inert atmosphere, most preferably under nitrogen or argon.

Examples of appropriate solvents include dichloromethane, trichloromethane, 1,2-dichloroethane, trichloroethene, benzene, toluene, xylene, halobenzenes, cymene, tetrahydrofuran, tert-butylmethylether, dimethoxyethane, diethylether, tert-butanol and mixtures thereof, which may eventually contain protic cosolvents and/or moisture. However, it is preferred to work under aprotic conditions.

In a more preferred set-up, solvents with low-coordination ability such as toluene, xylene, cymene, dichloromethane, trichloromethane or 1,2-dichloroethane are used as solvents under aprotic conditions.

The preferred catalysts or catalyst-precursors are based on ruthenium complexes of the general type I (M=Ru). A preferred choice of the following descriptors independently comprises: L, $L_1$=PPh$_3$, Pi-Pr$_3$, PCy$_3$ (i-Pr=isopropyl, Cy=cyclohexyl); X, $X_1$=halogen; R, $R_1$=H, CH=CPh$_2$, aryl, which may be substituted with C1–C5 alkyl, C1–C5 alkoxy, nitro, amino, halogen or a phenyl group. In an even more preferred embodiment: L=$L_1$=PCy$_3$, X, $X_1$=Cl, R=H, $R_1$=Ph or CH=CPh$_2$.

The ratio of catalyst to diolefin is not critical and can range from 1:5 to about 1:30000, preferably in the range of 1:20 to 1:2000.

The concentration of the substrate (molarity, M) in the given solvent should be low, usually ≦0.1M, since dimer and oligomer formation competes with the macrocyclization reaction at high concentrations. The reactions are usually carried out by adding a solution of the substrate to a solution of the chosen catalyst at such a rate that the propensity of cyclization of the respective substrate is larger than that of a reactive encounter of two substrate molecules. Alternatively, the solutions of substrate and the catalyst can be combined with low feeding rates in an appropriate reactor. In a more preferred set-up the final concentration of the substrate is <0.05M.

All kinds of dienes with 14 or more chain atoms may serve as the substrates, although the reaction rates and the conversions are usually decreasing with increasing substitution. Preferred substrates are dienes bearing monosubstituted alkene entities, which lead to the release of ethene as the by-product of the RCM process. In order to decrease the solubility of ethene in the chosen solvent, argon or nitrogen gas can be bubbled through the reaction mixture. This may beneficially influence the reaction rate and the isolated yields.

Work-up of the reaction mixtures and purification is not critical and follows routine techniques depending on the respective properties of the products formed and/or of the unreacted starting material. This may proceed either by distillation, filtration, chromatography, sublimation, crystallization, extraction as the preferred techniques. The products alkenes may be obtained as pure (E)-isomers, pure (Z)-isomers, or as a mixture of both.

The process pertains to the synthesis of macrocyclic esters (X=Y=O), amides (Y=O, X=NR$^1$), ethers (X=O, Y=R, R), or amine derivatives (X=NR$^2$, Y=R, R) of the general type VII with ring sizes (x) of 12≦x≦30, from appropriately substituted diene precursors including substrates that are devoid of any element of conformational preorganization

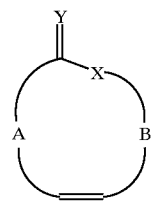

VII where A stands for a chain of n (CR$_2$) groups and B stands for a chain of m (CR$_2$) groups, each (CR$_2$) group of which may be replaced by a heteroatom Z. The substituents R on the carbon atoms of the ring may be identical or not identical and independently selected among hydrogen, C1–C20 alkyl, aryl, alkoxy, alkenyloxy, alkynyloxy, alkoxycarbonyl, perfluoroalkyl, cyano, halogen, oxo, alkylthio, arylthio, silyl, which can be optionally substituted with C1–C10 alkyl, aryl, oxo, halogen. The other descriptors can be independently selected from: n, m=1–25, with n+m=26; Z=O, NR$^3$, S; The substituents R$^1$, R$^2$, R$^3$ may be identical or not identical and independently selected among hydrogen, C1–C20 alkyl, aryl, acyl, alkoxycarbonyl, perfluoroalkyl, sulfonyl, R$_3$Si, which can be optionally substituted with C1–C10 alkyl, aryl, oxo, halogen. The method also pertains to products of the abovementioned types having geminal substituents on carbon atoms as well as to macrocyclic products that are anellated to one or more pre-existing carbo- or heterocyclic rings, independent of whether these are aromatic or non-aromatic. Representative examples are compiled in Tables 1–4.

This includes pentadecenolides (oxacyclohexadecen-2-ones) having the double bond at different positions in the ring which show valuable olfactory properties (for examples see Table 1). All of these products lead after hydrogenation to pentadecanolide (Exaltolid®) which is used as a musk-odored perfumary ingredient [Fürstner, A. et al., *J. Org. Chem.* 1996, 61, 3942–3943]. Di-unsaturated acyclic esters of the general type VIII are used as the starting materials, where the following descriptors are independently selected from: n, m=1–11, such that n+m=12; R$^1$, R$^2$, R$^3$, R$^4$ may be identical or not identical and independently chosen among hydrogen, C1–C10 alkyl; in a more preferred embodiment: R$^1$=R$^2$=R$^3$=R$^4$=H, n≧3.

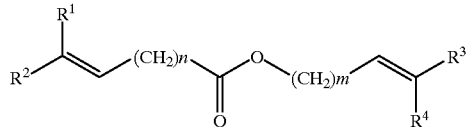

VIII

This includes the preparation of racemic or enantiomerically pure pentadecenolides and homologues thereof substituted at the non-olefinic sites of the ring by one or more C1–C10 alkyl, aryl, alkoxy, alkenyloxy, alkynyloxy, alkoxycarbonyl, perfluoroalkyl, alkylthio, arylthio, silyl groups, which can be optionally substituted with C1–C10 alkyl, aryl, halogen, or by one or more oxo, halogen or cyano groups or derivatives thereof (e.g. 20, 22, Table 2). Appropriately substituted products of this type are of interest to perfumary.

This includes the preparation of 7-hexadecen-16-olide 12 (Table 2), a valuable perfumary ingredient (Ambrettolid®), from substrates of the general type VIII, where n=5, m=8, R$^1$, R$^2$, R$^3$, R$^4$ may be identical or not identical and independently chosen among hydrogen, C1–C10 alkyl; in a more preferred embodiment: $R^1=R^2=R^3=R^4=H$. Double bond isomers of Ambrettolid can also be accessed.

This includes the synthesis of compound 16 (Table 2) and double bond isomers thereof which can be prepared in either racemic or enantiomerically pure form. Hydrogenation of these products affords 13-methyl-1-oxacyclotetradecan-2-one, a naturally occuring musk-odored lactone.

This includes the preparation of macrolactones which are known to act as pheromones (e.g. 14, 24, Table 2).

This includes the preparation of 1,6-dioxacycloheptadecen-2-ones and homologues thereof (e.g. 36, 38, Table 3) which may have the double bond at different positions within the ring. They lead after hydrogenation to 1,6-dioxacycloheptadecan-2-one or homologues respectively, which can be used as non-natural musk-odored perfume ingedients.

This includes the preparation of orsellinic acid type macrolides such as 32 and 34 in either racemic or enantiomerically pure form, which can be converted into the antibiotics lasiodiplodin and zearalenone (Table 3) [Furstner, A. et al. *Tetrahedron Lett.* 1996, 7005–7008; Kindler, N., *Ph.D. Thesis*, University of Dortmund, 1996].

This includes the preparation of racemic or enantiomerically pure azamacrolides such as epilachnene 30 and other components of insect defense secretions [Attygalle, A. B. et al., *Proc. Natl. Acad. Sci. USA*, 1993, 90, 5204–5208] and similar macrocyclic lactones containing nitrogen atoms within the macrocyclic ring which may either be N-protected by a suitable substituent or protonated (e.g. 26, 28, Table 3).

This pertains to the preparation of macrocyclic products of the abovementioned types having two or more ester, amide or ether groups as part of the ring. More specifically, this includes the preparation of 1,4-dioxahexadecen-5,16-diones which may have the double bond at different positions within the ring (e.g. 40, Table 3). After hydrogenation all of these products afford 1,4-dioxahexadecan-5,16-dione (ethylenebrassylate, Musk 144®).

The present method also pertains to the synthesis of macrocyclic ketones of the general type IX and derivatives thereof, with ring sizes of $12 \leq x \leq 30$, from appropriately substituted diene precursors including substrates that are devoid of any element of conformational preorganization

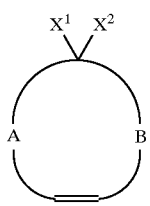

IX where A stands for a chain of n $CR_2$ groups and B stands for a chains of m $CR_2$ groups, each $CR_2$ group of which may be replaced by a heteroatom Z. The substituents R on the carbon atoms of the ring may be identical or not identical and independently chosen among hydrogen, C1–C20 alkyl, aryl, alkoxy, alkenyloxy, alkynyloxy, alkoxycarbonyl, perfluoroalkyl, cyano, oxo, halogen, alkylthio, arylthio, sulfonyl, silyl, which can be optionally substituted with C1–C10 alkyl, aryl, oxygen, halogen. The other descriptors can be independently selected from: n, m=1–25, with n+m= 26; $X^1$, $X^2$=O, $OR^1$, $SR^2$, $NR^3$, CN, halogen; Z=O, $NR^4$, S; The substituents $R^1$, $R^2$, $R^3$, $R^4$ may be identical or not identical and independently chosen among hydrogen, C1–C20 alkyl, acyl, aryl, alkoxycarbonyl, perfluoroalkyl, silyl, sulfonyl, which can be optionally substituted with C1–C10 alkyl, aryl, oxo, halogen. The method also pertains to products of the abovementioned types having geminal substituents on carbon atoms as well as to macrocyclic products that are anellated to one or more pre-existing carbo- or heterocyclic rings, independent of whether these are aromatic or non-aromatic.

This includes the preparation of cyclopentadecenones having the double bond at different sites within the ring (e.g. compound 42, Table 4). All of these products lead after hydrogenation to pentadecanone, which is a perfume ingredient. Di-unsaturated acyclic ketones of the general type X are used as the starting materials, where the following descriptors are independently selected from: n, m=1–11, with n+m=12; $R^1$, $R^2$, $R^3$, $R^4$ can be identical or not identical and independently chosen among hydrogen, C1–C10 alkyl; in a more preferred embodiment: $R^1=R^2=R^3=R^4=H$ and n, $m \geq 3$.

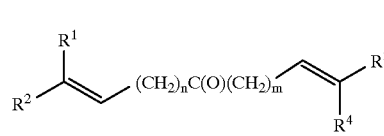

X

This includes the preparation of civetone (44, Table 4) from substrates of the general type X where n=m=7; $R^1$, $R^2$, $R^3$, $R^4$ can be identical or not identical and independently chosen among hydrogen, C1–C10 alkyl; in a more preferred embodiment: $R^1=R^2=R^3=R^4=H$.

This includes the preparation of macrocyclic diketones (e.g. compound 46, Table 4) from two molecules of acyclic ketones of the general type X via dimerization/RCM (cyclodimerization). The following descriptors are independently selected from: n, m=1–7, with n+m=8; $R^1$, $R^2$, $R^3$, $R^4$ can be identical or not identical and independently chosen among hydrogen, C1–C10 alkyl; in a more preferred embodiment: $R^1=R^2=R^3=R^4=H$ and n, $m \geq 3$.

EXAMPLES

Abbreviations used: Cy=cyclohexyl; i-Pr=isopropyl, Ph=phenyl

The following examples set forth the synthesis of mono- and polyfunctional macrocyclic rings by ring closing metathesis (RCM) of suitable diene precursors including those substrates that are devoid of any conformational preorganization. They also set forth the preferred embodiments of the present invention. Further examples compiled in Tables 1–4 have been prepared according to these representative procedures. Further objectives and advantages of the present invention not mentioned above will become apparent from the examples which are not intended to limit the scope of the present invention.

EXAMPLE 1

Synthesis of (E)-12-Methyl-oxacyclododec-8-en-2-one (Recifeiolide) (24). A solution of diene 23 (260 mg, 1.16 mmol) in $CH_2Cl_2$ (40 mL) and a solution of ruthenium carbene $Cl_2(PCy_3)_2RuCHCH=CPh_2$ (36 mg, 3 mol %) in $CH_2Cl_2$ (40 mL) were simultaneously added dropwise over a period of 24 h with vigorous stirring to $CH_2Cl_2$ (30 mL) at reflux temperature under argon. The solvent was removed in vacuo and the residue was purified by flash chromatography with hexane/ethyl acetate (30:1) as eluent to afford the lactone as a colorless syrup (191 mg, 80%). $^1$H NMR (200 MHz, CDCl$_3$) δ 5.47–5.01 (m, 3H), 2.38–1.67 (m, 7H), 1.52–1.09 (m, 10H). IR (film) 2976, 2934, 2855, 1731, 1449, 1365, 1349, 1320, 1268, 1249, 1225, 1187, 1159, 1122, 1079, 1046, 976, 962, 947, 829, 762, 709.

EXAMPLE 2

Synthesis of Oxacyclohexadec-11-en-2-one (2). A solution of diene 1 (298 mg, 1.12 mmol) in CH$_2$Cl$_2$ (100 mL) and a solution of ruthenium carbene Cl$_2$(PCy$_3$)$_2$RuCHCH=CPh$_2$ (50 mg, 5 mol %) in CH$_2$Cl$_2$ (100 mL) were simultaneously added dropwise over a period of 24 h with vigorous stirring to CH$_2$Cl$_2$ (50 mL) at ambient temperature under nitrogen. After stirring for another 6 h the solvent was removed in vacuo and the residue was purified by flash chromatography with hexane/ethyl acetate (100:1) as eluent to afford the lactone as a colorless syrup (219 mg, 79%). $^1$H NMR (200 MHz, CDCl$_3$) δ 5.45–5.28 (m, 2H), 4.18–4.07 (m, 2H), 2.37–2.29 (m, 2H), 2.10–2.00 (m, 4H), 1.72–1.54 (m, 4H), 1.49–1.30 (m, 10H). IR (film) 3000, 2928, 2856, 1736, 1461, 1385, 1346, 1252, 1234, 1168, 1152, 1113, 1085, 1024, 969, 719.

EXAMPLE 3

Synthesis of Oxacyclohexadec-6-en-2-one (4). A solution of diene 3 (300 mg, 1.13 mmol) in CHCl$_3$ (100 mL) and a solution of ruthenium carbene Cl$_2$(PCy$_3$)$_2$RuCHCH=CPh$_2$ (50 mg, 5 mol %) in CHCl$_3$ (100 mL) were simultaneously added dropwise over a period of 24 h with vigorous stirring to CHCl$_3$ (50 mL) at ambient temperature. After stirring for another 6 h the solvent was removed in vacuo and the residue was purified by flash chromatography with hexane/ethyl acetate (150:1) as eluent to afford the lactone as a colorless syrup (173 mg, 62%). $^1$H NMR (200 MHz, CDCl$_3$) δ 5.36–5.16 (m, 2H), 4.08–4.05 (m, 2H), 2.28 (t, 2H, J=7.2), 2.09–1.92 (m, 4H), 1.71–1.55 (m, 4H), 1.28–1.24 (m, 12H). IR (film) 3005, 2934, 2850, 1738, 1452, 1350, 1254, 1240, 1170, 969, 714.

EXAMPLE 4

Synthesis of Oxacyclohexadec-6-en-2-one (4). A solution of diene 3 (300 mg, 1.13 mmol) in CHCl$_3$ (100 mL) and a solution of ruthenium carbene Cl$_2$(PCy$_3$)$_2$Ru=CHPh (4.6 mg, 0.5 mol %) in CHCl$_3$ (10 mL) were simultaneously added dropwise over a period of 24 h with stirring to CHCl$_3$ (50 mL) at ambient temperature. After stirring for another 6 h the solvent was removed in vacuo and the residue was processed as described above providing the lactone as colorless syrup (195 mg, 70%). Analytical data as compiled above.

EXAMPLE 5

Synthesis of Oxacycloheneicos-11-en-2-one (18). A solution of diene 17 (300 mg, 0.89 mmol) in toluene (100 mL) and a solution of ruthenium carbene Cl$_2$(PCy$_3$)$_2$RuCHCH=CPh$_2$ (41 mg, 5 mol %) in toluene (100 mL) were simultaneously added dropwise over a period of 24 h with vigorous stirring to toluene (50 mL) at 80° C. After stirring for another 10 h at that temperature the solvent was removed in vacuo and the residue was purified by flash chromatography with hexane/ethyl acetate (200:1) as eluent to afford the lactone as a colorless syrup (195 mg, 71%). $^1$H NMR (200 MHz, CDCl$_3$) δ 5.44–5.28 (m, 2H), 4.11 (td, 2H, J=5.6, 1.7), 2.31 (t, 2H, J=6.4), 2.03–1.98 (m, 4), 1.68–1.58 (m, 4H), 1.45–1.23 (m, 22H). IR (film) 3001, 2926, 2854, 1737, 1462, 1385, 1348, 1252, 1236, 1175, 1117, 1090, 1066, 1030, 969, 722.

EXAMPLE 6

Synthesis of (13R)-(+)-13-Methyl-oxacyclotetradec-8-en-2-one (16). A solution of diene 15 (150 mg, 0.59 mmol) in CH$_2$Cl$_2$ (50 mL) and a solution of ruthenium carbene Cl$_2$(PCy$_3$)$_2$RuCHCH=CPh$_2$ (27 mg, 5 mol %) in CH$_2$Cl$_2$ (50 mL) were simultaneously added dropwise over a period of 20 h with vigorous stirring to CH$_2$Cl$_2$ (30 mL) at ambient temperature. After stirring for another 3 h the solvent was removed in vacuo and the residue was purified by flash chromatography with hexane/ethyl acetate (30:1) as eluent to afford the lactone as a colorless syrup (102 mg, 72%). $^1$H NMR (200 MHz, CDCl$_3$) δ 5.29–5.24 (m, 2H), 4.06 (dd, 1H, J=10.8, 3.5), 3.81 (dd, 1H, J=10.8, 9.2), 2.37–2.30 (m, 2H), 2.11–1.18 (m, 15H), 0.89 (d, 3H, J=6.8). IR (film): 3024, 2929, 2856, 1734, 1461, 1444, 1378, 1341, 1252, 1206, 1168, 1148, 1116, 1007, 970, 737.

EXAMPLE 7

Synthesis of Oxacyclopentadec-8-ene (54). A solution of diene 53 (300 mg, 1.26 mmol) in CH$_2$Cl$_2$ (50 mL) and a solution of ruthenium carbene Cl$_2$(PCy$_3$)$_2$RuCHCH=CPh$_2$ (58 mg, 5 mol %) in CH$_2$Cl$_2$ (50 mL) were simultaneously added dropwise over a period of 15 h with vigorous stirring to CH$_2$Cl$_2$ (50 mL) at reflux temperature. After stirring for another 10 h at that temperature the solvent was removed in vacuo and the residue was purified by flash chromatography with hexane/diethyl ether (100:1) as eluent to afford the ether as a colorless syrup (179 mg, 67%). $^1$H NMR (200 MHz, CDCl$_3$) δ 5.33–5.20 (m, 2H), 3.36–3.32 (m, 4H), 2.02–1.98 (m, 4H), 1.51–1.47 (m, 4H), 1.37–1.29 (m, 12H). IR (film) 3025, 2925, 2854, 2795, 1672, 1488, 1460, 1436, 1411, 1372, 1352, 1117, 1020, 967, 866, 702.

EXAMPLE 8

Synthesis of Cyclopentadecen-8-one (42). A solution of diene 41 (120 mg, 0.48 mmol) in CH$_2$Cl$_2$ (30 mL) and a solution of ruthenium carbene Cl$_2$(PCy$_3$)$_2$RuCHCH=CPh$_2$ (9 mg, 2 mol %) in CH$_2$Cl$_2$ (30 mL) were simultaneously added dropwise over a period of 20 h with vigorous stirring to CH$_2$Cl$_2$ (30 mL) at reflux temperature under argon. After stirring for another 12 h at that temperature, the solvent was removed in vacuo and the residue was purified by flash chromatography with hexane/ethyl acetate (30:1) as eluent to afford the ketone as a colorless syrup (77 mg, 72%). $^1$H NMR (200 MHz, CDCl$_3$) δ 5.38–5.19 (m, 2H), 2.40 (t, 4H, J=5.9), 2.04–2.01 (m, 4H), 1.71–1.59 (m, 4H), 1.43–1.10 (m, 12 H). IR (film) 2927, 2854, 1713, 1460, 1440, 1409, 1365, 1120, 971, 730, 702.

EXAMPLE 9

Synthesis of 16-Trifluoromethyl-oxacyclohexadec-11-en-2-one (20). A solution of diene 19 (300 mg, 0.90 mmol) in CH$_2$Cl$_2$ (50 mL) and a solution of ruthenium carbene Cl$_2$(PCy$_3$)$_2$RuCHCH=CPh$_2$ (41 mg, 5 mol %) in CH$_2$Cl$_2$ (50 mL) were simultaneously added dropwise over a period of 48 h with vigorous stirring to CH$_2$Cl$_2$ (50 mL) at reflux temperature. After stirring for another 24 h the solvent was removed in vacuo and the residue was purified by flash chromatography with hexane/diethyl ether (100:1) as eluent to afford the lactone as a pale yellow syrup (220 mg, 80%). $^1$H NMR (200 MHz, CDCl$_3$) δ 5.47–5.22 (m, 3H), 2.57–2.31 (m, 2H), 2.15–1.85 (m, 4H), 1.82–1.30 (m, 16H). IR (film) 2930, 2857, 1755, 1461, 1442, 1398, 1367, 1284, 1236, 1179, 1129, 1096, 1046, 971, 927, 698.

EXAMPLE 10

Synthesis of 12-Propyl-13-aza-oxacyclopentadec-6-en-2-one (Epilachnene) (30). A solution of HCl in THF (273 μL, 0.62 M) was added to diene 27 (R=H) (50 mg, 0.17 mmol) in THF (5 mL). The solvent was removed in vacuo and the residue (i.e. 29, dissolved in $CH_2Cl_2$ (30 mL)) was simultaneously added dropwise at ambient temperature with a solution of the ruthenium carbene $Cl_2(PCy_3)_2RuCHCH=CPh_2$ (8 mg, 5 mol %) in $CH_2Cl_2$ (30 mL) to $CH_2Cl_2$ (20 mL) over a period of 28 h. After stirring for another 12 h the solvent was removed in vacuo and the residue was neutralized with sat. $NaHCO_3$. The aqueous phase was extracted twice with ether, the combined organic layers were dried ($Na_2SO_4$) and evaporated to dryness. Final purification was achieved by flash chromatography (neutral alumina, hexane/ethylacetate 10:1) as eluent to give the azamacrolide as a colorless syrup (38 mg, 84%). $^1$H NMR (400 MHz, $CDCl_3$) δ 5.38–5.21 (m, 2H), 4.33–4.26 (m, 1H), 4.01–3.93 (m, 1H), 3.00–2.86 (m, 1H), 2.78–2.68 (m, 1H), 2.47–2.27 (m, 4H), 2.18–2.07 (m, 2H), 2.02–2.01 (m, 2H), 1.84–1.77 (m, 1H), 1.72–1.65 (m, 1H), 1.48–1.10 (m, 10H), 0.87 (t, 3H, J=8.0). IR (film) 3446, 3359, 2955, 2928, 2855, 1739, 1684, 1458, 1439, 1384, 1260, 1204, 1158, 1082, 1019, 969, 806, 699.

EXAMPLE 11

Synthesis of Azacyclooctadec-11-en-2-one (52). A solution of diene 51 (200 mg, 0.68 mmol) in $CH_2Cl_2$ (50 mL) was added dropwise over a period of 48 h to a solution of ruthenium carbene $Cl_2(PCy_3)_2RuCHCH=CPh_2$ (0.32 mg, 0.05 mol %) in $CH_2Cl_2$ (30 mL) with vigorous stirring at reflux temperature. After stirring another 48 h at that temperature the solvent was removed in vacuo and the residue was recrystallized to afford the lactam as colorless crystals (150 mg, 83%). Mp 106.5–107.0° C. $^1$H NMR (200 MHz, $CDCl_3$) δ 5.79–5.67 (m, 1H), 5.49–5.22 (m, 2H), 3.35–3.21 (m, 2H), 2.22–2.14 (m, 2H), 2.10–1.98 (m, 4H), 1.64–1.17 (m, 20 H). IR (KBr) 3300, 3085, 3003, 2923, 2849, 2684, 1639, 1552, 1461, 1434, 1360, 1267, 1243, 1193, 1123, 1082, 1026, 966, 909, 726, 610.

EXAMPLE 12

(R)-(+)-2,4-Dimethoxy-7-methyl-7,8,9,10,11,14-hexahydro-6-oxa-benzocyclododecen-5-one (32). Solutions of diene 31 (100 mg, 0.30 mmol) and of $Cl_2(PCy_3)_2RuCHCH=CPh_2$ (17 mg, 6 mol %) in $CH_2Cl_2$ (31 mL each) were separately slowly added to $CH_2Cl_2$ (62 mL) over a period of 24 hours while a low stream of argon was constantly bubbled through the reaction mixture. The mixture was stirred at ambient temperature until thin layer chromatography indicated complete conversion of the substrate. Evaporation of the solvent and flash chromatography of the residue afforded a fraction of the title compound consisting of the pure (E)-isomer (56 mg, 61%) and another fraction consisting of a mixture of the (E)- and the (Z)-isomer (30 mg, 33%). Selected data for the (E)-isomer: $[\alpha]_D^{20}$=+72 (c 0.46, acetone). IR: 2972, 2932, 2866, 2843, 1714, 1604, 1586, 1490, 1458, 1422, 1376, 1328, 1284, 1262, 1228, 1208, 1161, 1133, 1107, 1094, 1047, 971, 899, 883, 848, 831, 779, 744, 727, 640, 622. $^1$H-NMR (300 MHz, $CDCl_3$): δ=6.34 (d, 1 H, $^4$J=2.3), 6.32 (d, 1 H, $^4$J=2.3), 5.41 (dddd, 1 H, $^3$J=14.9, 10.2, 4.5, $^4$J=1.9), 5.20 (dddd, 1 H, $^3$J=14.9, 10.2, 3.2, $^4$J=1.6), 5.10 (dqd, 1 H, $^3$J=10.0, 6.3, 2.8), 3.80 (s, 3 H), 3.78 (s, 3 H), 3.36 (d, 1 H, $^3$J=6.3), 3.07 (ddd, 1 H, $^3$J=14.2, $^2$J=5.0, $^4$J=2.9), 2.22 (m, 1 H), 1.21–1.71 (br. m, 6 H), 1.31 (d, 3 H, $^3$J=6.2), 1.09 (m, 1 H). $^{13}$C-NMR (75 MHz, $CDCl_3$): δ=168.05, 161.06, 158.33, 140.78, 132.70, 128.70, 117.63, 107.10, 96.90, 68.75, 55.97, 55.33, 38.28, 34.63, 32.79, 24.71, 20.13, 19.98. MS (EI): m/z (rel. intensity): 304 (24) [M$^+$], 217 (10), 207 (100), 205 (15), 204 (10), 196 (32), 191 (11), 189 (10), 178 (12). $C_{18}H_{24}O_4$ (304.38): calcd. C 71.03, H 7.95; found C 71.52, H 7.71; HRMS: calcd. 304.167460, found 304.167393.

EXAMPLE 13

Cyclodimerization: Synthesis of Docosa-6,17-diene-1,12-dione (46). Solutions of diene 45 (350 mg, 1.8 mmol) and of $Cl_2(PCy_3)_2RuCHCH=CPh_2$ (50 mg, 3 mol %) in $CH_2Cl_2$ (50 mL each) were simultaneously added dropwise to refluxing $CH_2Cl_2$ (30 mL) over a period of 20 h under argon. The solvent was removed in vacuo and the residue purified by flash chromatography to give diketone 46 as colorless crystals (217 mg, 72%). mp=80–83° C. $^1$H NMR (200 MHz, $CDCl_3$) δ 5.32–5.39 (m, 4H), 2.33–2.43 (m, 8H), 2.08–1.99 (m, 8H), 1.48–1.62 (m, 8H) 1.28–1.39 (m, 8H). IR (KBr): 3030, 2989, 2930, 2851, 1705, 1667, 1459, 1438, 1411, 1383, 1357, 1296, 1276, 1209, 1106, 1069, 1004, 967, 729, 706.

EXAMPLE 14

Synthesis of 1,4-Dioxahexadec-10-en-5,16-dione (40). Solutions of diene 39 (250 mg, 0.89 mmol) and of $Cl_2(PCy_3)_2RuCHCH=CPh_2$ (16 mg, 2 mol %) in $CH_2Cl_2$ (40 mL each) were slowly dropped into boiling CH2Cl2 (30 mL) over a period of 12h. For work-up the solvent was evaporated and the residue purified by flash chromatography affording dilactone 40 as plesently smelling, colorless crystals (198 mg, 87%). mp=46–47. $^1$H NMR (200 MHz, $CDCl_3$) δ 5.39–5.21 (m, 2H), 4.30 (s, 1H), 4.27 (s, 3H), 2.37–2.26 (m, 4H), 2.11–2.02 (m, 4H), 1.71–1.55 (m, 4H), 1.48–1.38 (m, 4H). IR: 2931, 2854, 1733, 1462, 1439, 1398, 1371, 1296, 1275, 1257, 1223, 1169, 1102, 1072, 1035, 965, 874.

TABLE 1

Catalytic Ring Closing Metathesis: Typical Examples for the Preparation of Pentadecenolides from Different Dienes Using Complexes of Type I as Catalyst Precursors

| Substrate | Product (Yield %) |
|---|---|
| 1 | 2 (79%) |

TABLE 1-continued

Catalytic Ring Closing Metathesis: Typical Examples for the Preparation of Pentadecenolides from Different Dienes Using Complexes of Type I as Catalyst Precursors

| Substrate | Product (Yield %) |
|---|---|
| 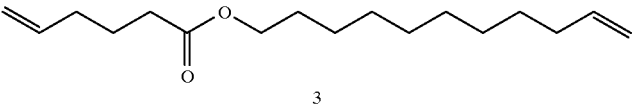 3 | 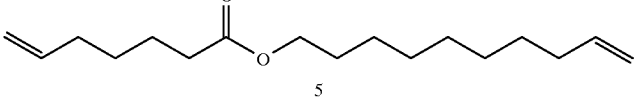 4 (62%) |
| 5 | 6 (76%) |
| 7 | 8 (80%) |
| 9 | 10 (80%) |

TABLE 2

Typical Examples of Macrocylic Lactones Prepared by RCM of Different Dienes Using Complexes of Type I as Catalyst Precursors

| Substrate | Product (Yield %) |
|---|---|
| 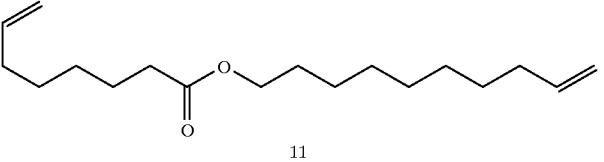 11 | 12 (78%) |

TABLE 2-continued
Typical Examples of Macrocylic Lactones Prepared by RCM of Different Dienes Using Complexes of Type I as Catalyst Precursors
| Substrate | Product (Yield %) |
|---|---|
| 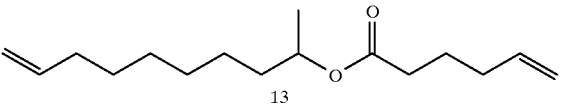 13 | 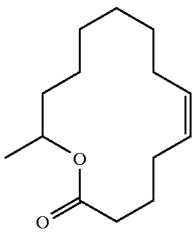 14 (71%) |
| 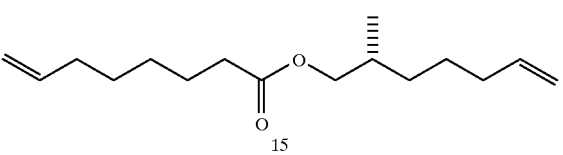 15 | 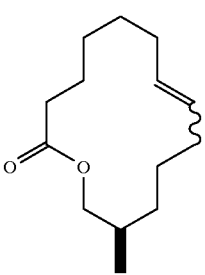 16 (72%) |
| 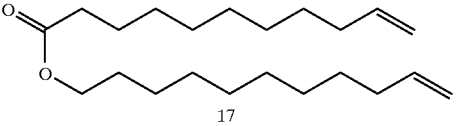 17 | 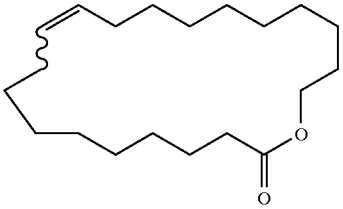 18 (71%) |
| 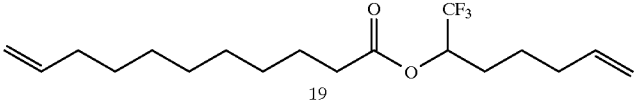 19 | 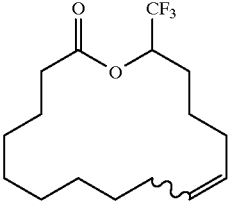 20 (80%) |
| 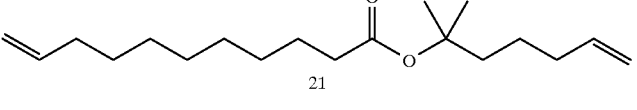 21 | 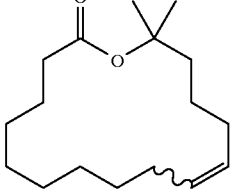 22 (72%) |
| 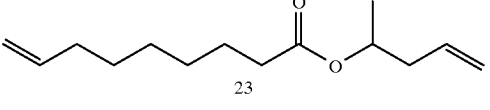 23 | 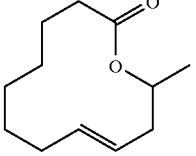 24 (80%) |

TABLE 3
Functionalized Macrocycles by RCM Using Complexes of Type I as Catalyst Precursors.
BOC = COOtBu; FMOC = 9-fluorenylmethoxycarbonyl; Ts = p-tosyl.
| Substrate | Product (Yield %) |
|---|---|
| 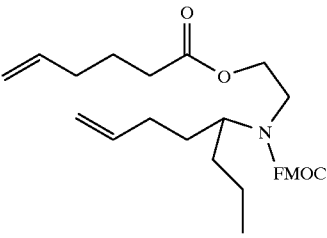 25 | 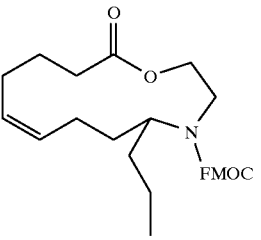 26 (83%) |
| 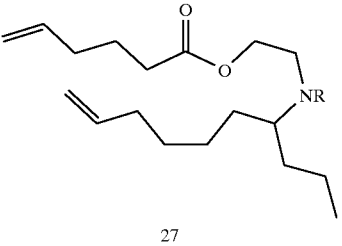 27 | 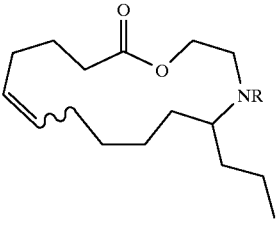 28<br>R = BOC (89%)<br>R = FMOC (92%)<br>R = COCF$_3$ (94%)<br>R = Ts (80%) |
| 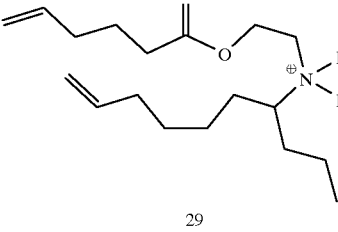 29 | 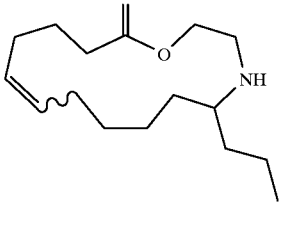 30 (84%) |
| 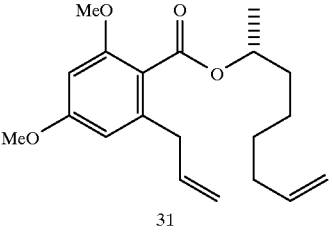 31 | 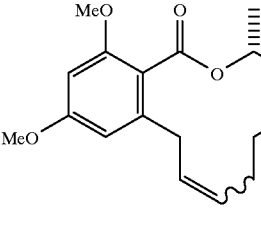 32 (94%) |
| 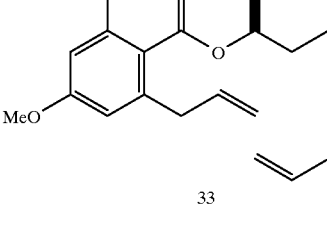 33 | 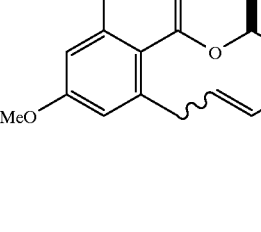 34 (80%) |
| 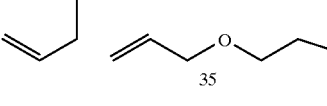 35 | 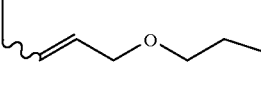 36 (76%) |

TABLE 3-continued

Functionalized Macrocycles by RCM Using Complexes of Type I as Catalyst Precursors.
BOC = COOtBu; FMOC = 9-fluorenylmethoxycarbonyl; Ts = p-tosyl.

| Substrate | Product (Yield %) |
|---|---|
| 37 | 38 (80%) |
| 39 | 40 (87%) |

TABLE 4

Functionalized Macrocycles by RCM Using Complexes of Type I as Catalyst Precursors.

| Substrate | Product (Yield %) |
|---|---|
| 41 | 42 (72%) |
| 43 | 44 (75%) |
| 45 | 46 (72%) |
| 47 | 48 (88%) [a] |

TABLE 4-continued

Functionalized Macrocycles by RCM Using Complexes of Type I as Catalyst Precursors.

| Substrate | Product (Yield %) |
|---|---|
| 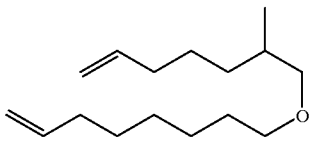 49 | 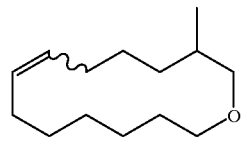 50 (74%) |
| 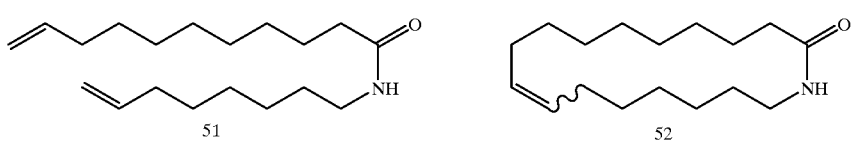 51 | 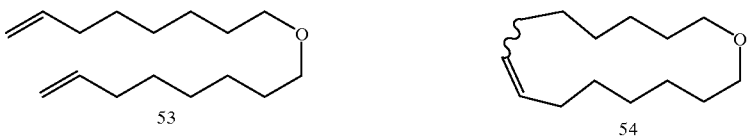 52 (83%) |
| 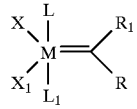 53 | 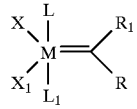 54 (67%) |

[a] based on converted starting material.

We claim:

1. A process for preparing a macrocycle comprising a ring consisting of 12–30 ring atoms and at least one polar functional group selected from the group consisting of a polar ring heteroatom or a polar substituent on the ring, said process comprising subjecting a substrate comprising a diene precursor of said macrocycle to a catalytic ring closing metathesis reaction in the presence of a catalyst or catalyst precursor of the formula I:

$$\begin{array}{c} X \diagdown \overset{L}{\underset{|}{M}} \diagup R_1 \\ X_1 \diagup \overset{|}{\underset{L_1}{\phantom{M}}} \diagdown R \end{array} \quad I$$

wherein
M represents Ru or Os;
R and $R_1$ independently represent hydrogen or alkenyl, alkynyl, alkyl, aryl, alkoxy, alkenyloxy, or alkoxycarbonyl, each of which has 2 to 20 carbon atoms and is optionally substituted by alkyl having 1 to 5 carbon atoms, halogen, alkoxy having 1 to 5 carbon atoms, or phenyl optionally substituted by halogen, nitro, amino, or alkyl or alkoxy, each having 1 to 5 carbon atoms;
X and $X_1$ independently represent an anionic ligand; and
L and $L_1$ independently represent a neutral electron donor; wherein said diene precursor does not comprise an element of conformational preorganization that predisposes the diene precursor to ring closure, wherein said element of conformational preorganization that predisposes the diene precursor to ring closure is selected from the group consisting of hydrogen bonding, rigid backbones and supramolecular ensembles.

2. The process according to claim 1, wherein said polar functional group is selected from the group consisting of a polar ring heteroatom or a polar substituent on the ring, and said polar substituent on the ring is selected from the group consisting of an ester group, an ether group, an epoxide group, a silyl ether group, a silylketene acetal group, a thioacetal group, an acylal group, an anhydride group, a thioether group, an imine group, a silylenol ether group, an amine group, an ammonium salt group, an amide group, a nitrile group, a perfluoroalkyl group, a halogen atom, an alcohol group, a ketone group, an aldehyde group, a carbamate group, a carbonate group, a urea group, a sulfonate group, a sulfone group, a disubstituted alkene group, a trisubstituted alkene group, a tetrasubstituted alkene group, and a nitro group.

3. The process according to claim 1, wherein in the catalyst or catalyst precursor of formula I, X and/or $X_1$ is halogen.

4. The process according to claim 1, wherein in the catalyst or catalyst precursor of formula I, L and/or $L_1$ is phosphine, sulfonated phosphine, phosphite, arsine, stibine or amine.

5. The process according to claim 4, wherein in the catalyst or catalyst precursor of formula I, L and/or $L_1$ is trialkylphosphine where at least one of the alkyl groups is secondary alkyl or cycloalkyl.

6. The process according to claim 1, wherein the catalyst or catalyst precursor of formula I is $Cl_2(PCy_3)_2RuCHCH=CPh_2$ or $Cl_2(PCy_3)_2Ru=CHPh$.

7. A process according to claim 1, which is for the formation of a macrocyclic product of the formula VII:

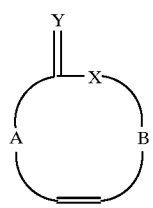

VII wherein

A represents —$(CR_2)_n$—; and

B represents —$(CR_2)_m$—;

wherein n and m independently represents an integer from 1–25 with the proviso that the sum of n+m≦26; and each R is independently selected from the group consisting of hydrogen, alkyl having 1 to 20 carbon atoms, aryl, alkoxy, alkenyloxy, alkynyloxy, alkoxycarbonyl, perfluoroalkyl, cyano, halogen, oxo, alkylthio, arylthio, or silyl, which can be optionally substituted with alkyl having 1 to 10 carbon atoms, aryl, oxo, or halogen; or one or more ($CR_2$) groups may be replaced by a heteroatom Z;

wherein z represents O, S or $NR^3$; and $R^3$ represents hydrogen, alkyl having 1 to 20 carbon atoms, aryl, acyl, alkoxycarbonyl, perfluoroalkyl, sulfonyl, or $R_3Si$, which is optionally substituted by alkyl having 1 to 10 carbon atoms, aryl, oxo or halogen;

x represents O, $NR^1$ or $NR^2$; and

Y represents O or $R_2$;

wherein $R^1$ and $R^2$ are identical or different and independently represent hydrogen, alkyl having 1 to 20 carbon atoms, aryl, acyl, alkoxycarbonyl, perfluoroalkyl, sulfonyl, or $R_3Si$, which is optionally substituted by alkyl having 1 to 10 carbon atoms, aryl, oxo or halogen;

said process comprising subjecting a diene precursor of said macrocycle to a ring closing metathesis reaction in the presence of a catalyst or catalyst precursor of the formula I as set forth in claim 1.

8. The process according to claim 7, wherein the macrocyclic products of the formula VII have geminal substituents on carbon atoms and/or are anellated to one or more aromatic or non-aromatic pre-existing carbo- or heterocyclic rings.

9. The process according to claim 7, wherein the macrocyclic products are pentadecenolides (oxacyclohexadecen-2-ones) or 1,6-dioxacycloheptadecen-2-ones or 1,4-dioxahexadecan-5,6-diones, all of which may have the double bond at different sites within the macrocyclic ring, or 7-hexadecen-16-olide.

10. A process according to claim 1, which is for the formation of a macrocyclic product of the formula IX:

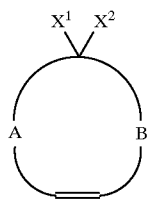

IX wherein

A represents —$(CR_2)_n$—; and

B represents —$(CR_2)_m$—;

wherein n and m independently represents an integer from 1–25 with the proviso that the sum of n+m≦26; and each R is independently selected from the group consisting of group consisting of hydrogen, alkyl having 1 to 20 carbon atoms, aryl, alkoxy, alkenyloxy, alkynyloxy, alkoxycarbonyl, perfluoroalkyl, cyano, halogen, oxo, alkylthio, arylthio, sulfonyl or silyl, which can be optionally substituted with alkyl having 1 to 10 carbon atoms, aryl, oxo, or halogen; or one or more ($CR_2$) groups may be replaced by a heteroatom Z;

wherein

Z represents O, S or $NR^4$; and $R^4$ represents hydrogen, alkyl having 1 to 20 carbon atoms, aryl, acyl, aryl, alkoxycarbonyl, perfluoroalkyl, silyl, or sulfonyl, which is optionally substituted by alkyl having 1 to 10 carbon atoms, aryl, oxo or halogen; and $X^1$ and $X^2$ are identical or different and independently represent O, $OR^1$, $SR^2$, $NR^3$, CN or halogen;

wherein $R^1$, $R^2$ and $R^3$ are identical or different and independently represent hydrogen, alkyl having 1 to 20 carbon atoms, aryl, acyl, aryl, alkoxycarbonyl, perfluoroalkyl, silyl, or sulfonyl, which is optionally substituted by alkyl having 1 to 10 carbon atoms, aryl, oxo or halogen;

said process comprising subjecting a diene precursor of said macrocycle to a ring closing metathesis reaction in the presence of a catalyst or catalyst precursor of the formula I as set forth in claim 1.

11. The process according to claim 10, wherein the products of the formula IX have geminal substituents on carbon atoms and/or are anellated to one or more pre-existing aromatic or non-aromatic carbo- or heterocyclic rings.

12. The process according to claim 10, where the products are the homologeous series of cycloalkenones of 12–30 carbon atoms having the double bond at different positions within the ring.

13. The process according to claim 1, wherein the dienes are dimerized before ring closure, resulting in a cyclodimerization.

14. The process according to claim 1, wherein the ring closing metathesis is carried out at temperatures between −20° C. to about 125° C., preferably between 0° C. and 90° C.

15. The process according to claim 1, wherein the molar ratio of the catalyst to diene is in the range from 1:5 to about 1:30000.

16. The process according to claim 1, where the final molarity of the substrate is below 0.1M.

17. A multi-step process for the preparation of an olfactory compound, a perfumery ingredient, a pheromone, a crown ether, or an antibiotic, wherein one of the steps of said multi-step process comprises preparation of a macrocycle according to a process according to claim 1.

18. The process according to claim 15, wherein the molar ratio of the catalyst to diene is in the range from 1:20 to 1:2000.

19. The process according to claim 16, wherein the final molarity of the substrate is below 0.05 M.

* * * * *